United States Patent [19]

Mishima et al.

[11] Patent Number: 5,077,059
[45] Date of Patent: Dec. 31, 1991

[54] PROCESS FOR PREPARING MELANOGENIC INHIBITOR, AND PIGMENTATION-LIGHTENING AGENT CONTAINING THE SAME

[75] Inventors: Yuyaka Mishima, Sowa-cho, Nadaku, Kobe-shi, Hyogo; Yasuaki Oyama, Fukuoka; Masashi Kurimoto, Okayama, all of Japan

[73] Assignees: Mishimazo Yuaka, Kukuoka; Seibutsu Kagaku Kenkyujo, Okayama; Sansho Seiyaku Kabushiki Kaisha, Hyogo, all of Japan; Sansho Seiyaku Kabushiki Kaisha, Hyogo, all of Japan

[21] Appl. No.: 288,260

[22] Filed: Dec. 22, 1988

[30] Foreign Application Priority Data

Dec. 29, 1987 [JP] Japan ................................ 62-336470

[51] Int. Cl.$^5$ .......................... A61K 35/12; A61K 7/40
[52] U.S. Cl. ..................................................... 424/573
[58] Field of Search ...................... 424/62, 93, 95, 573; 435/41, 240.2

[56] References Cited

PUBLICATIONS

Sigi et al, "Inhibition of DNA and Protein Synthesis in Melanocytes by a Melanoma Extract" CA80:131386, 1974.
Ishikawa, Kebal "Inhibition of Aminoacyl–Transfer RNA Formation by Low–Molecular Substances from Melanoma Extract", CA100:116579, 1984.
Ohyama, Y. "Topical Agents for Inhibiting Melanin Generation" CA107:12943, 1987.
J Cell Physiol 137 (1), 1988-35-44 Kameyama K; Montague P M; Hearing VJ.
Isolation and Characterization of Tyrosinase Inhibitors and their Differential Action on Melanogenic Subcellular Compartments in Amelanotic and Melanotic Melanomas; British Journal of Dermatology (1980); 625–633 Imokawa G and Mishima Y.
Loss of Melanogenic Properties in Tyrosinases Induced by Glycosylation Inhibitors within Malignant Melanoma Cells; Cancer Research vol. 42 (1982) 1994–2002.
GERL–Coated Vesicle System in the Melanin Synthesizing Cell: Its three-Dimensional Ultrastructure and Tyrosinase Activity, Nippon Hifuka Gakkai Zasshi (1977) 87(13) 883–901.

*Primary Examiner*—Douglas W. Robinson
*Assistant Examiner*—Jean C. Witz
*Attorney, Agent, or Firm*—Browdy and Neimark

[57] ABSTRACT

The present invention relates to a process for preparing a melanogenic inhibitor and a pigmentation-lightening agent containing the same, more particularly, the present invention relates to a process for preparing a novel melanogenic inhibitor which is obtained by proliferating an established cell line from a warm-blooded animal, homogenizing the proliferated cells and recovering the same from the resultant homogenate, as well as to a pigmentation-lightening agent containing the same.

10 Claims, No Drawings

PROCESS FOR PREPARING MELANOGENIC INHIBITOR, AND PIGMENTATION-LIGHTENING AGENT CONTAINING THE SAME

BACKGROUND OF THE INVENTION

1. Field of the Invention

The present invention relates to a process for preparing a melanogenic inhibitor and a pigmentation-lightening agent containing the same, more particularly, the present invention relates to a process for preparing a novel melanogenic inhibitor which is obtained by proliferating an established cell line from a warm-blooded animal, homogenizing the proliferated cells and recovering the same from the resultant homogenate, as well as to a pigmentation-lightening agent containing the same.

2. Description of the Prior Art

Melanin is present in the deeper part of the skin and plays an important role in the protection of the body from the affects of ultraviolet rays. Melanin is an important factor in medical science and cosmetology. It has been known that melanin is synthesized in the skin tissue. The presence of excessive melanin makes the skin dark and unhomogeneous distribution of melanin therein causes chloasma and ephelis. Such symptoms are important factors in cosmetology.

Conventionally, tyrosinase inhibitors, for example, vitamin C, glutathione and cysteine, have been used in order to decrease the level of melanin in the skin, as well as to produce a pigmentation-lightened skin.

Conventional tyrosinase inhibitors are unfavorably stable and insufficient in their efficacy in producing a pigmentation-lightened skin via viable cells. Hydroquinone and MBEH (monobezyl ether of hydroquinone), which exert a high efficacy in realizing a pigmentation-lightened skin, have been used as tyrosinase inhibitors, but they also inhibit the inherent physiological function of the skin, as well as causing side effects, for example, alphos, pigmentary disorder and contact dermatitis.

SUMMARY OF THE INVENTION

The present inventors have studied substances that inhibit the melanogenesis in the skin by using the function of viable cells, and that exert an efficacy in realizing a pigmentation-lightened skin but not direct inhibition of tyrosinase activity. As a result, the present inventors found that a novel melanogenic inhibitor which substantially does not inhibit tyrosinase activity, but exhibits melanogenic- inhibitory- and dopa-reaction-inhibitory-activities in a prescribed pigment cell is obtainable by proliferating a transferable warm-blooded animal cell (referred to as "established cell line" hereinafter) in vitro or proliferating the established cell line while supplying a nutrient body fluid of a non-human warm-blooded animal to the established cell line, homogenizing the proliferated cells, and recovering the melanogenic inhibitor from the resultant homogenate.

DETAILED DESCRIPTION OF THE INVENTION

The present invention relates to a process for preparing a melanogenic inhibitor and a pigmentation-lightening agent containing the same, more particularly, the present invention relates to a process for preparing a novel melanogenic inhibitor which is obtained by proliferating an established cell line from a warm-blooded animal, homogenizing the proliferated cells and recovering the same from the resultant homogenate, as well as to a pigmentation-lightening agent containing the same.

Any established cell line used in the process for preparing melanogenic inhibitor according to the present invention can be freely employed insofar as it readily proliferates in vitro or proliferates while receiving a nutrient body fluid of a non-human warm-blooded animal, and it produces the melanogenic inhibitor. Examples of such established cell lines include those derived from warm-blooded animals, available from Dainippon Pharmaceutical Co., Ltd., Tokyo, Japan, or those available from American Type Culture Collection, 12301 Parklawn Drive, Rockville, Md. 20852-1776, and those established cell lines can be favorably selected.

Particularly, those derived from melanomas, for example, A-375 (ATCC CRL 1619), C32 (ATCC CRL 1585), C32TG (ATCC CRL 1579), G-361 (ATCC CRL 1424), WM-115 (ATCC CRL 1675), WM266-4 (ATCC CRL 1676), Clone M-3 (ATCC CCL 53.1), $D_1$178, FF (ATCC CRL 1479), RPMI 1846 (ATCC CCL 49), Hs 294T (ATCC HTB 140), Hs 695T (ATCC HTB 137), HT-144 (ATCC HTB 63), Malme-3M (ATCC HTB 64), RPMI-7951 (ATCC HTB 66), SK-MEL-1 (ATCC HTB 67), SK-MEL-5 (ATCC HTB 70) and SK-MEL-28 (ATCC HTB 72); those derived from leukemia, for example, BecII, Bri7, EB-3 (ATCC CCL 85), OF (ATCC CRL 1646), L1210 (ATCC CCL 219), CCFR-CEM (ATCC CCL 119), HL-60 (ATCC CCL 240), MOLT-3 (ATCC CRL 1552), IM-9 (ATCC CCL 159), KG-1 (ATCC CCL 246), Raji (ATCC CCL 86), K-562 (ATCC CCL 243), Daudi (ATCC CCL 213), Namalwa (ATCC CRL 1432), Ramos (ATCC CRL 1596), BC3A (ATCC TIB 60), A20 (ATCC TIB 208), C1498 (ATCC TIB 49), $P388D_1$ (ATCC CCL 46), WR19L (ATCC TIB 52), and P815 (ATCC TIB 64); and those obtained by treating normal cells with viruses, agents or irradiation, can be favorably used in the invention.

In order to accelerate the growth rate of the established cell lines and to increase the production of melanogenic inhibitor per cell, a gene which encodes the function of the production of melanogenic inhibitor in the established cell lines can be treated with the methods, for example, cell fusion using polyethylene glycol and Sendai virus; and recombinant techniques using enzymes, for example, DNA ligase, nuclease and DNA polymerase. The description of established cell lines is not intended to limit the scope of the invention.

These established cell lines can be proliferated in vitro or in vivo while supplying a nutrient body fluid of a non-human warm-blooded animal to them.

Preferably, the established cell lines are proliferated by directly implanting in the body of a non-human warm-blooded animal, or inoculating into a diffusion chamber for proliferation while supplying a nutrient body fluid of a non-human warm-blooded animal to them.

The in vivo proliferation has the additional advantages that it cuts or considerably reduces the need for a nutrient culture medium containing an expensive serum; that it reduces cares during cell proliferation; that it stabilizes cell proliferation; and that it augments the production of melanogenic inhibitor per cell.

The established cell lines can be easily proliferated by the in vivo proliferation by implanting them in a non-human warm-blooded animal or placing them in a diffusion chamber in which the established cell lines can be supplied with the nutrient body fluid of the animal, and feeding the animal in usual way.

Furthermore, the in vivo proliferation results in a more stable cell proliferation, a higher cell growth rate, a larger amount of proliferated cells, and a larger amount of melanogenic inhibitor than in vitro proliferation.

The non-human warm-blooded animals usable in the in vivo proliferation are those in which established cell lines proliferate; for example, fowls such as chicken and pigeon, and mammals such as dog, cat, monkey, rabbit, goat, pig, horse, cow, guinea pig, rat, nude rat, hamster, mouse, and nude mouse.

Since implantation of an established cell line may elicit an undesirable immunoreaction in the animal, the use of an animal in the possible youngest stage, for example, egg, embryo or fetus, or newborn or infant animal, is desirable in order to reduce the immunoreaction to the possible lowest level.

With the same purpose, the animal may be irradiated with x-rays or gamma-rays, about 200-600 rem, or injected with an antiserum or an immunosuppressant prior to implantation.

When nude mouse or nude rat is used, an established cell line from a non-human warm-blooded animal of the same class or order, as well as that of the same species or genus can be implanted without pretreatment and proliferated readily with less fear of causing undesirable immunoreaction because nude mouse and nude rat elicit less immunoreaction even in their adulthood.

The established cell line can be implanted in any site of the animal as long as the established cell line proliferates in the site: for example, in the allantoic cavity, intravenously, intraperitoneally or subcutaneously.

Alternatively, the established cell line can be proliferated by placing it in conventional diffusion chamber of various shapes and sizes, equipped with an appropriate means which excludes the animal cell but supplies the nutrient body fluid of a non-human warm-blooded animal to the established cell line, for example, membrane-filter, ultrafilter or hollow fiber, pore size of about $10^{-7}$-$10^{-5}$ m; embedding, for example, intraperitoneally, the chamber in a non-human warm-blooded animal; and allowing the established cell line to proliferate in the chamber while allowing the established cell line to receive the nutrient body fluid of the animal.

The diffusion chamber can be arranged and placed, for example, on the animal, in such manner that the nutrient body fluid in the diffusion chamber can freely circulate therethrough. The diffusion chamber can be arranged in such manner that the culture can be observed during the cell proliferation through the chamber wall, and/or that the diffusion chamber can be replaced at intervals with a fresh one to continue the cell proliferation over the life span of the animal without sacrifice, as well as to greatly augment the cell production per animal.

Since in the method using diffusion chamber the established cell lines never contact with the animal cell and elicit much lower levels of undesirable immunoreaction, any non-human warm-blooded animal can be freely used without pretreatment to reduce immunoreaction and the proliferated cells can be easily recovered.

The animal is fed in usual manner, and no special care is required even after implantation. The period for maximum cell proliferation is usually from 1 to 10 weeks.

The number of the obtained cells is about $10^7$-$10^{12}$ or more cells per animal.

More particularly, according to the invention, the implanted established cell line increases by about $10^2$-$10^7$-fold or more, which is about $10$-$10^6$-fold or higher than that attained by inoculating and proliferating the established cell line on in vitro proliferation. This is very favorable for preparation of the melanogenic inhibitor.

The melanogenic inhibitor derived from the proliferated cells can be easily purified, separated and recovered by the following process: The proliferated cells are homogenized by the method, for example, destruction, ultrasonication, and freezing-thawing method. The resultant homogenate is then centrifuged and membrane-filtered to remove undissolved substances. The supernatant or filtrate containing the melanogenic inhibitor is concentrated and dried.

When the melanogenic inhibitor should be purified to a much higher level, the conventional methods, for example, adsorption and desorption with ion-exchange, gel filtration, electrophoresis, ion-exchange chromatography, high-performance liquid chromatography, and column chromatography are employable in order to obtain the possible highest purity of melanogenic inhibitor.

The purified melanogenic inhibitor has the following properties:

(a) Action

Substantially not inhibiting tyrosinase activity, but exhibiting both melanogenic-inhibitory- and dopa-reaction-inhibitory-activities in a prescribed pigment cell:

(b) Molecular weight 100-500 daltons on gel filtration;

(c) Ultraviolet absorption spectrum

Exhibiting no specific maximum absorption;

(d) Thermal stability

Stable at 100° C. for 5 minutes, but losing its activity in a prescribed pigment cell at 600° C. for 2 hours;

(e) pH stability

Stable at pH 2.0 or 11.0 at 4° C. for 16 hours;

(f) Solubility in solvent

Dissolvable in water and methanol; and (g) Color

Colorless or pale yellow in aqueous solution.

Several of the activities described in the specification are detected by the following methods.

The tyrosinase activity is detected by the method described in *British Journal of Dermatology*, Vol. 103, pp. 625-633 (1980).

The melanogenic inhibitory activity in a prescribed pigment cell is detected by the method described in *Cancer Research*, Vol. 42, pp. 1994-2002 (1982).

B-16 cell derived from mouse melanoma is suspended in 10 ml Eagle's minimal essential medium (Grand Island Biological Co., Grand Island, N.Y.), supplemented with 10% fetal calf serum, to give $4 \times 10^4$ cells. The suspension is placed into a 25 cm² Roux's flask, and cultured at 37° C. with 5% $CO_2$. The cultivation is continued for 5 days while replacing the culture medium with a fresh one supplemented with a melanogenic inhibitor specimen at the first- and third-days. After completion of the culture, the resultant cells are washed with a phosphate buffer (pH 7.2) containing 0.8 w/v % saline to detach them from the inside wall of the Roux's flask by the addition of a solution containing trypsin and EDTA (ethylenediaminetetraacetic acid), collected on a filter paper, and dried. The resultant cells are subjected to densitometry to measure the reflection light at a wave length of 500 nm, followed by determination of the reflection absorbance (degree of darkness).

One unit of melanogenic inhibitory activity is defined as the amount of the melanogenic inhibitor which halves the reflection absorbance of B-16 cells without treatment of melanogenic inhibitor.

Dopa-reaction inhibitory activity is detected by the method described in *Japanese Journal of Dermatology*, Vol. 87, No. 13, pp. 883-901 (1977). B-16 cell derived from mouse melanoma is cultured in the presence of melanogenic inhibitor for 5 days according to the above method. After the cell is whitened, the culture medium is removed and the cell is fixed in 10 v/v % formaldehyde solution. The fixed cell is then soaked in 0.1M phosphate buffer containing 0.1 w/v % l.-dopa, followed by 3-hour standing at 37° C. Dopa-reaction inhibitory activity is detected by the fact that the cell do not become dark.

Since the present melanogenic inhibitor is very safe and highly stable, it can be used in a pigmentation-lightening pharmaceutical agents, for example, injection, internal medicine, medicine for external application, and bath liquid: and in cosmetics, for example, milky lotion, pack, and cream. The pigmentation-lightening agent exerts a prophylactic and therapeutic effect on chromatosis, for example, chloasma, ephelis, and sunburn.

The present invention will hereinafter be explained in more detail with the following Experiments.

EXPERIMENT-1

Process for Preparing Melanogenic Inhibitor

Newborn hamsters were injected with an antiserum prepared by conventional method to reduce possible immunoreaction, implanted subcutaneously with G-361 human melanoma cell, and fed in usual way for 3 weeks. The tumor masses formed subcutaneously in the hamsters were extracted, added with 4 volumes of water, and fed to a homogenizer. The resultant homogenate was centrifuged, and the supernatant was subjected to ion-exchange chromatography using DEAE-Sephacel®, a product of Pharmacia LKB Biotechnology AB, Uppsala, Sweden, to fractionate a melanogenic inhibitor with 10 mM phosphate buffer (pH 6.8). The fractions were pooled, concentrated, and subjected to gel filtration chromatography using Toyo Peal® HW40, a product of Toyo Soda Mfg. Co., Ltd., Tokyo, Japan, to collect fractions that exhibited melanogenic inhibitory activity, and that had a molecular weight of 100-500 daltons. The fractions were pooled, concentrated, and lyophilized to obtain a solid specimen containing the melanogenic inhibitor.

The product exhibited a melanogenic inhibitory activity of about 4.2 units/mg on the dry solid basis (referred to as "d.s.b." hereinafter), and the yield was about 650 units per 100 g of G-361 cell.

(a) Action

Substantially not inhibiting tyrosinase activity, but exhibiting both melanogenic-inhibitory- and dopa-reaction-inhibitory-activities in a prescribed pigment cell;

(b) Molecular weight 100-500 daltons on gel filtration:

(c) Ultraviolet absorption spectrum

Exhibiting no specific maximum absorption:

(d) Thermal stability

Stable at 100° C. for 5 minutes, but losing its activity in a prescribed pigment cell at 600° C. for 2 hours;

(e) pH stability

Stable at pH 2.0 or 11.0 at 4° C. for 16 hours;

(f) Solubility in solvent

Dissolvable in water and methanol; and (g) Color

Colorless or pale yellow in aqueous solution.

Based on the above, the melanogenic inhibitor according to the present invention is novel and different from conventional tyrosinase inhibitors, for example, vitamin C, glutathione and cysteine.

EXPERIMENT 2

Comparison of Melanogenic Inhibitory Activity

According to the method for detecting melanogenic inhibitory activity in a prescribed pigment cell, specimens containing 1 or 3 units of an intact melanogenic inhibitor, obtained by the method in Experiment 1, were used to compare melanogenic inhibitory activity in established melanoma cell lines, i.e., B-16 cell (mouse melanoma origin), RPMI 1846 cell (hamster melanoma origin), and Malme-3M cell (human melanoma origin).

As control, either a system without melanogenic inhibitor or another system with melanogenic inhibitor which had been treated at 600° C. for 2 hours was tested similarly as above.

Every prescribed pigment cell, which had been added with the specimen containing the intact melanogenic inhibitor, exhibited a significant melanogenic inhibitory activity, as well as an efficacy in realizing a pigmentation-lightened skin, in proportion to the amount of the melanogenic inhibitor.

In this Experiment, vitamin C, glutathione, and cysteine, which were known as tyrosinase inhibitor, exhibited no melanogenic inhibition.

EXPERIMENT 3

Acute Toxicity Test

Acute toxicity of a melanogenic inhibitor obtained by the method in Experiment 1 was tested with 20-day old mice. The acute toxicity of the melanogenic inhibitor was extremely low, and its $LD_{50}$ on intraperitoneal injection was 5,000 units or more in terms of melanogenic inhibitory activity in a prescribed pigment cell.

As evident from the above, the present melanogenic inhibitor exerts a strong melanogenic inhibitory activity, i.e., a high efficacy in realizing a pigmentation-lightened skin, to melanomas of the same class or order, as well as those of the same species or genus, and is extremely safe from the viewpoint of its effective dose.

The present pigmentation-lightening agent containing the melanogenic inhibitor is be used at a dose of 0.001-10,000 units/day/adult; preferably, 0.001-100 units in systemic administrations such as intramuscular injection; 0.01-1,000 units in oral administrations such as internal medicine: 0.1-10,000 units in percutaneous or permucosal administrations, for example, medicine for external applications, and bath liquids, and cosmetics such as milky lotion and cream. The dose is dependent on the route of administration of the pigmentation-lightening agent and/or patient's symptom.

Such pigmentation-lightening agent containing the melanogenic inhibitor alone, or, if necessary, in combination with other materials, for example, biologically-active substances, nutrients, bases, and vehicles, is selected according to the use and form of pharmaceuticals and cosmetics. The pigmentation-lightening agent can be used in the prevention or treatment of local chromatosis such as chloasma, ephelis and sunburn, as well as of systemic chromatosis such as Addisonism.

For example, the pigmentation-lightening agent can be used in the form of injections such as those in liquid or lyophilized-powder which is dissolved in a solvent such as water prior to its use; in the form of oral agents such as those in liquid, powder, granule, capsule, and tablet: in the form of percutaneous agents such as those in liquid, milky lotion, cream and ointment; in the form of medicine for external application such as those in cataplasm which are applied on their on side with an agent such as cream; in the form of bath liquids: and in the form of cosmetics such as lotion, milky lotion, pack, and cream. The melanogenic activity of the pigmentation-lightening agent can be promoted by iontophoresing the melanogenic inhibitor into deeper part of the skin. If necessary, such iontophoresis can be accelerated by using a supporting electrolyte.

If necessary, the melanogenic inhibitor can be freely used in combination with one or more members of vitamin C, vitamin E, glutathione, cysteine, kojic acid, placenta extract, glucosamine derivative(s), "PIONIN (KANKOH-SO No. 201)", a product of Nippon Kankoh-Shikiso Kenkyusho, Co., Ltd., Okayama, Japan, colloidal sulfur, and hydroquione derivative(s) in order to promote the melanogenesis inhibition and to realize a pigmentation-lightened skin. Sunscreen agent can be suitably used in combination with the pigmentation-lightening agent to promote its efficacy.

The preparation of the melanogenic inhibitor according to the present invention will be explained by the following Examples A.

EXAMPLE A-1

(Namalwa cell derived from human leukemia) was inoculated to Eagle's minimal essential medium (pH 7.4) supplemented with 20% fetal calf serum, and subjected to conventional in vitro suspension culture at 37° C.

After completion of the culture, the resultant cells were centrifugally collected, and fed to a homogenizer. The resultant homogenate was purified by membrane-filtration, ion-exchange chromatography and gel filtration, after which the resultant was concentrated, sterilized by heating, and membrane-filtered to obtain a solution containing a melanogenic inhibitor.

The product exhibited a melanogenic inhibitory activity of about 0.6 units/mg in a prescribed pigment cell, d.s.b., and the yield was about 50 units per 100 g of Namalwa cell.

The product can be used in a pigmentation-lightening pharmaceutical agent, for example, in the form of injection, oral agent, external preparation, and bath liquid, and in cosmetics, for example, in the form of milky lotion, pack, and cream because it exerts a high efficacy in realizing a pigmentation-lightened skin in the prevention and treatment of local chromatosis such as chloasma, ephelis and sunburn, as well as of systemic chromatosis such as addisonism.

EXAMPLE A-2

RPMI 1846 cell derived from hamster melanoma was subcutaneously implanted in hamsters which were then fed in usual way. According to the method in Experiment 1, the tumor masses, subcutaneously formed in the hamsters, were extracted and fed to a homogenizer. The resultant homogenate was purified by membrane-filtration, ion-exchange chromatography, and gel filtration chromatography, concentrated, and sterilized by heating, and membrane-filtered, after which the resultant was dried in vacuo to obtain a solid specimen containing a melanogenic inhibitor.

The product exhibited a melanogenic inhibitory activity of about 3.2 units/mg in a prescribed pigment cell, d.s.b., and the yield was about 260 units per 100 g of RPMI 1846 cell.

Similarly as the product in Example A-1, the product can be used in a pigmentation-lightening agent directed to pharmaceutical and cosmetic uses because it exerts a high efficacy in realizing a pigmentation-lightened skin in the prevention and treatment of local and systemic chromatosis.

EXAMPLE A-3

SK-MEL-1 cell derived from human melanoma was intraperitoneally implanted in adult nude mice which were then fed in usual way for 4 weeks. The tumor masses, intraperitoneally occurred in the nude mice, were extracted, and treated similarly as the method in Example A-1 to obtain a solution containing a melanogenic inhibitor.

The product exhibited a melanogenic inhibitory activity of about 4.1 units/mg in a prescribed pigment cell, d.s.b., and the yield was about 460 units per 100 g of SK-MEL-1 cell.

Similarly as the product in Example A-1, the product can be used in a pigmentation-lightening agent directed to pharmaceutical and cosmetic uses because it exerts a high efficacy in realizing a pigmentation-lightened skin in the prevention and treatment of chromatosis.

EXAMPLE A-4

Clone M-3 cell derived from mouse melanoma was inoculated into an about 10 ml volumes of plastic cylindrical diffusion chamber equipped with a membrane filter, 0.5 micron in diameter. Physiological saline was injected to the diffusion chamber which was then intraperitoneally embedded into an adult rat, and fed in usual way for 4 weeks. The diffusion chamber was extracted to collect the proliferated cells, which were then treated similarly as in Example A-2 to obtain a solid specimen containing a melanogenic inhibitor.

The product exhibited a melanogenic inhibitory activity of about 3.3 units/mg in a prescribed pigment cell, d.s.b., and the yield was about 270 units per 100 g of Clone M-3 cell.

Similarly as the product in Example A-2, the product can be used in a pigmentation-lightening agent directed to pharmaceutical and cosmetic uses because it exerts a high efficacy in realizing a pigmentation-lightened skin in the prevention and treatment of chromatosis.

The following Examples B are examples of pigmentation-lightening agents which contain the present melanogenic inhibitor as the effective component. Specifically, the present melanogenic inhibitor derived from a warm-blooded animal can be advantageously used in the pigmentation-lightening agents.

EXAMPLE B-1

Injection

One part by weight of a melanogenic inhibitor, obtained by the method in Experiment 1, was dissolved in 200 parts by weight of physiological saline, and the mixture was membrane-filtered in usual manner. Two milliliter aliquots of the filtrate were distributed into sterilized glass vials, lyophilized, and hermetically sealed to obtain a lyophilized injection.

The injection is dissolved in sterile purified water, prior to its use.

The injection can be advantageously used as a pigmentation-lightening agent in the prevention and treatment of local chromatosis such as chloasma and ephelis, as well as of systemic chromatosis such as addisonism.

EXAMPLE B-2

Oral Agent (Tablet)

Three parts by weight of a melanogenic inhibitor, obtained by the method in Experiment 1, was homogeneously mixed with 82 parts by weight of maltose, 61 parts by weight of corn starch, and 4 parts by weight of sucrose fatty acid ester, and the mixture was tabletted in usual manner to obtain tablets, 150 mg weight each.

Similarly as the product in Example B-1, the tablet can be advantageously used as a pigmentation-lightening agent in the prevention and treatment of chromatosis.

EXAMPLE B-3

Oral Agent (Capsule)

One part by weight of a melanogenic inhibitor, obtained by the method in Example A-2, was homogeneously mixed with 147 parts by weight of maltose and 2 parts by weight of sucrose fatty acid ester. The mixture was fed to a granulator and the resultant was encapsulated in usual manner with gelatin to obtain capsules, 150 mg weight each.

Similarly as the product in Example B-1, the capsule can be advantageously used as a pigmentation-lightening agent in the prevention and treatment of chromatosis.

EXAMPLE B-4

Medicine for External Application (Ointment)

Five parts by weight of a melanogenic inhibitor, obtained by the method in Example A-2, was homogeneously mixed with 10.0 parts by weight of glycerine. To the mixture was added 50.0 parts by weight of petrolatum, 10.0 parts by weight of vegetable wax, 10.0 parts by weight of lanolin, 14.5 parts by weight of sesame oil, and 0.5 parts by weight of Japanese mint oil, and the resultant mixture was homogeneously mixed to obtain an ointment.

Similarly as the product in Example B-2, the ointment can be advantageously used as a pigmentation-lightening agent in the treatment of chromatosis, as well as in the prevention of sunburn.

EXAMPLE B-5

Medicine for External Application (Milky Lotion)

Five parts by weight of a melanogenic inhibitor, obtained by the method in Example A-1, was homogeneously mixed in usual manner with 12.0 parts by weight of liquid paraffine, 4.0 parts by weight of lanolin, 3.5 parts by weight of oleic acid, 1.0 part by weight of triethanolamine, and 3.0 parts by weight of octyl dodecyl myristate. The mixture was added with small amounts of antiseptic and flavoring agent, and 71.5 parts by weight of purified water, and the resultant was homogenized to obtain a milky lotion.

Similarly as the product in Example B-4, the milky lotion can be advantageously used as a pigmentation-lightening agent in the prevention and treatment of chromatosis.

EXAMPLE B-6

Medicine for External Application (Lotion)

Two parts by weight of a melanogenic inhibitor, obtained by the method in Example A-3, was homogeneously mixed in usual manner with 1.0 part by weight of hydrogenated castor oil polyoxyethylene, 15.0 parts by weight of ethanol, 0.1 part by weight of citric acid, 0.3 parts by weight of sodium citrate, 4.0 parts by weight of 1,3-butylene glycol, 0.5 parts by weight of sodium pyrrolidonecarbonate, and small amounts of antiseptic and flavoring agent, and 77.0 parts by weight of purified water to obtain a lotion.

Similarly as the product in Example B-5, the lotion can be favorably used as a pigmentation-lightening agent in the prevention and treatment of chromatosis such as chloasma, ephelis and sunburn.

EXAMPLE B-7

Bath Liquid

One part by weight of a melanogenic inhibitor, obtained by the method in Example A-4, was mixed with 80 parts by weight of ethanol, and 19 parts by weight of purified water together with small amounts of coloring- and flavoring-agents to obtain a bath liquid.

The product is diluted in 100–10,000 volumes of hot water prior to the use in bath for the prevention and treatment of local and systemic chromatosis. The product exerts an efficacy in realizing a pigmentation-lightened skin even when diluted in solvents such as water, hot water or lotion, prior to use in washing face or in bath.

EXAMPLE B-8

Cosmetic (milky lotion)

A half part by weight of polyoxyethylene behenyl ether, 1.0 part by weight of polyoxyethylene sorbitol tetraoleate, 1.0 part by weight of lipophilic glyceryl monostearate, 0.5 parts by weight of stearic acid, 0.5 parts by weight of behenyl alcohol, 1.0 part by weight of avocado oil, and small amounts of vitamin E, antiseptic and flavoring agent were dissolved by heating in usual manner. To the mixture was added 1.0 part by weight of a melanogenic inhibitor obtained by the method in Experiment 1, 5.0 parts by weight of 1,3-buthylene glycol, 0.1 part by weight of carboxyvinylpolymer, and 85.3 parts by weight of purified water, and the resultant was homogenized to obtain a milky lotion.

The milky lotion can be used as a pigmentation-lightening agent in the prevention and treatment of chromatosis such as chloasma, ephelis and sunburn.

EXAMPLE B-9

Cosmetic (pack)

Two parts by weight of a melanogenic inhibitor, obtained by the method in Example A-3, was homogeneously mixed in usual manner with 1.5 parts by weight of squalene, 0.5 parts by weight of hydrogenated castor oil, 4.0 parts by weight of glyceride, 15.0 parts by weight of polyvinyl alcohol, 10.0 parts by weight of ethanol, and 67 parts by weight of purified water to obtain a pack.

Similarly as the product in Example B-8, the pack can be advantageously used as a pigmentation-lightening agent in the prevention and treatment of chromatosis.

EXAMPLE B-10

Cosmetic (cream)

Two parts by weight of polyoxyethylene glycol monostearate, 5 parts by weight of glyceryl monostearate SE, 5 parts by weight of stearic aid, 1 part by weight of behenyl alcohol, 1 part by weight of liquid paraffine, 10 parts by weight of glyceryl tri (2-ethylhexanoate), and small amounts of antiseptic and flavoring agent were dissolved by heating in usual manner. To the mixture was added 2 parts by weight of a melanogenic inhibitor, obtained by the method in Example A-4, 5 parts by weight of 1,3-buthylene glycol, and 75 parts by weight of purified water, and the resultant mixture was homogenized to obtain a cream.

Similarly as the product in Example B-8, the cream can be advantageously used as a pigmentation-lightening agent in the prevention and treatment of chromatosis.

EFFECT OF THE INVENTION

As described above, the present invention provides a process for preparing a novel melanogenic inhibitor which substantially does not inhibit tyrosinase activity, but exhibits both melanogenic-inhibitory- and dopa-reaction-inhibitory-activities in a prescribed pigment cell, as well as providing a pigmentation-lightening agent containing the melanogenic inhibitor as the effective component.

Since the present melanogenic inhibitor strongly inhibits melanogenesis and exerts a high efficacy in realizing a pigmentation-lightened skin, the melanogenic inhibitor can be used in pharmaceuticals, for example, injection, oral agent, medicine for external application, and bath liquid, and in cosmetics, for example, milky lotion, pack, and cream as a pigmentation-lightening agent in the prevention and treatment of local and systemic chromatosis such as chloasma, ephelis, sunburn and addisonism.

Furthermore, the present melanogenic inhibitor can be advantageously produced and used in the art that can be safely used in its effective dose, and that the heat sterilization and long preservation of the melanogenic inhibitor are very easy because it has high thermal- and pH-stabilities. The present melanogenic inhibitor is a significant substance in the art.

While there has been described what is at present considered to be the preferred embodiments of the invention, it will be understood that various modifications may be made therein, and it is intended to cover in the appended claims all such modifications as fall within the true spirits and scope of the invention.

We claim:

1. A process for preparing a melanogenic inhibitor, comprising:

either allowing an established cell line from a melanoma or leukemia selected from the group consisting of SK-MEL-1 (ATCC HTB 67) cell, RPMI 1846 (ATCC CCL 49) cell, Clone M-3 (ATCC CLL 53.1) cell and Namalwa (ATCC CRL 1432)cell; to proliferate in vitro; or allowing said established cell line to proliferate by implanting said established cell line in the body of a non-human warm-blooded animal or inoculating said established cell line into a diffusion chamber placed inside or outside the body of a non-human warm-blooded animal while supplying blood of a non-human warm-blooded animal to said established cell line;

homogenizing the proliferated cells and recovering from the resultant homogenate a substance which does not substantially inhibit tryosinase activity, but exhibits both melanogenic-inhibitory and dopa-reaction-inhibitory-activities in a prescribed pigment cell;

has a molecular weight of 100-500 daltons on gel filtration;

exhibits no specific maximum ultraviolet absorption;

is thermally stable at 100° C. for 5 minutes, but loses its activity in a prescribed pigment cell at 600° C. for 2 hours;

has a pH stability between about 2.0 to 11.0 at 4° C. for 16 hours;

is soluble in water and methanol; and is colorless or pale yellow in aqueous solution.

2. The process of claim 1, wherein said proliferated cells are homogenized by destruction, ultrasonication or freezing-thawing.

3. The process of claim 1, wherein said melanogenic inhibitor is recovered from the resultant homogenate by centrifugation, membrane-filtration, adsorption and desorption with ion-exchange, gel filtration, electrophoresis, ion-exchange chromatography, high-performance liquid chromatography or column chromatography.

4. The process of claim 1, wherein said non-human warm-blooded animal is fed over a period of 1 to 10 weeks.

5. A pigmentation-lightening composition containing a melanogenic inhibitor derived from a melanoma or leukemia selected from the group consisting of SK-MEL-1 (ATCC HTB 67) cell, RPMI 1846 (ATCC CCL 49) cell, Clone M-3 (ATCC CCL 53.1) cell and Namalwa (ATCC CRL 1432) cell that does not substantially inhibit tyrosinase activity, but exhibits both melanogenic-inhibitory- and dopa-reaction-inhibitory-activities in a prescribed pigment cell;

has a molecular weight of 100-500 daltons on gel filtration;

exhibits no specific maximum ultraviolet absorption;

is thermally stable at 100° C. for 5 minutes, but loses its activity in a prescribed pigment cell at 600° C. for 2 hours;

has a pH stability between about 2.0 to 11.0 at 4° C. for 16 hours;

is soluble in water and methanol; and is colorless or pale yellow in aqueous solution.

6. The pigmentation-lightening composition of claim 5, wherein said composition is used in a pharmaceutical.

7. The pigmentation-lightening composition of claim 6, wherein said pharmaceutical is in the form of an injection, tablet, capsule, ointment, lotion or milky lotion.

8. The pigmentation-lightening composition of claim 6, wherein a dose of said pharmaceutical is in the range of 0.001-10,000 units/days/adult.

9. The pigmentation-lightening composition of claim 5, wherein said agent is used in a cosmetic.

10. The pigmentation-lightening composition of claim 9, wherein said cosmetic is in the form of a bath liquid, lotion, milky lotion, pack or cream.

* * * * *

UNITED STATES PATENT AND TRADEMARK OFFICE
CERTIFICATE OF CORRECTION

PATENT NO. : 5,077,059
DATED : Dec. 31, 1991
INVENTOR(S) : MISHIMA et al.

It is certified that error appears in the above-identified patent and that said Letters Patent is hereby corrected as shown below:

On the title page,
    Column 1, Section [75], delete "Yuyaka Mishima" and insert therefore --Yutaka Mishima--; and Column 1, Section [73], delete the designation of the assignees in its entirety and insert therefore --KABUSHIKI KAISHA HAYASHIBARA SEIBUTSU KAGAKU KENKYUJO, Okayama; SANSHO SEIYAKU KABUSHIKI KAISHA, Kukuoka; YUTAKA MISHIMA, Hyogo; all of Japan---.

Signed and Sealed this

Twenty-eighth Day of December, 1993

Attest:

BRUCE LEHMAN

*Attesting Officer*     *Commissioner of Patents and Trademarks*